(12) United States Patent
Horsley

(10) Patent No.: US 9,333,127 B1
(45) Date of Patent: May 10, 2016

(54) BODILY GARMENT ASSEMBLY

(71) Applicant: Debra A. Horsley, Coppell, TX (US)

(72) Inventor: Debra A. Horsley, Coppell, TX (US)

( * ) Notice: Subject to any disclaimer, the term of this patent is extended or adjusted under 35 U.S.C. 154(b) by 315 days.

(21) Appl. No.: 13/857,255

(22) Filed: Apr. 5, 2013

(51) Int. Cl.
*A61F 13/505* (2006.01)
*A61F 13/68* (2006.01)
*A61F 13/76* (2006.01)

(52) U.S. Cl.
CPC ............... *A61F 13/68* (2013.01); *A61F 13/505* (2013.01); *A61F 13/76* (2013.01)

(58) Field of Classification Search
CPC ......... A61F 13/72; A61F 13/74; A61F 13/76; A61F 13/505; A61F 13/15268; A61F 2013/15276
USPC .................... 604/396, 397, 398, 402, 385.14
See application file for complete search history.

(56) References Cited

U.S. PATENT DOCUMENTS

| | | | |
|---|---|---|---|
| 2,016,355 A * | 10/1935 | Alsop | 604/396 |
| 3,509,881 A | 5/1970 | Sabee | |
| 3,828,785 A | 8/1974 | Gamm et al. | |
| 4,338,939 A * | 7/1982 | Daville | 604/399 |
| 4,928,323 A * | 5/1990 | Nathan | 2/406 |
| D309,022 S | 7/1990 | Vigmo | |
| 5,069,672 A * | 12/1991 | Wippler et al. | 604/385.14 |
| 5,290,270 A | 3/1994 | Fisher | |
| 5,360,422 A * | 11/1994 | Brownlee et al. | 604/385.15 |
| 5,669,902 A * | 9/1997 | Sivilich | 604/396 |
| 5,700,256 A | 12/1997 | Yamamoto et al. | |
| 6,616,645 B1 * | 9/2003 | Moravek | 604/385.06 |
| 2002/0016580 A1 * | 2/2002 | Wada | A41B 9/004 604/385.24 |
| 2004/0158225 A1 | 8/2004 | Coates | |
| 2004/0230175 A1 * | 11/2004 | Rainville-Lonn et al. | 604/396 |
| 2015/0007382 A1 * | 1/2015 | Akerley | 2/406 |

* cited by examiner

*Primary Examiner* — Lynne Anderson

(57) ABSTRACT

A bodily garment assembly includes a sleeve that may be worn around a user's waist so the sleeve covers the user's crotch. An absorbing member is removably coupled to the sleeve so the absorbing member abuts the user's crotch. The absorbing member may absorb urine.

7 Claims, 2 Drawing Sheets

BODILY GARMENT ASSEMBLY

BACKGROUND OF THE DISCLOSURE

Field of the Disclosure

The disclosure relates to bodily garment devices and more particularly pertains to a new bodily garment device for absorbing urine.

SUMMARY OF THE DISCLOSURE

An embodiment of the disclosure meets the needs presented above by generally comprising a sleeve that may be worn around a user's waist so the sleeve covers the user's crotch. An absorbing member is removably coupled to the sleeve so the absorbing member abuts the user's crotch. The absorbing member may absorb urine.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
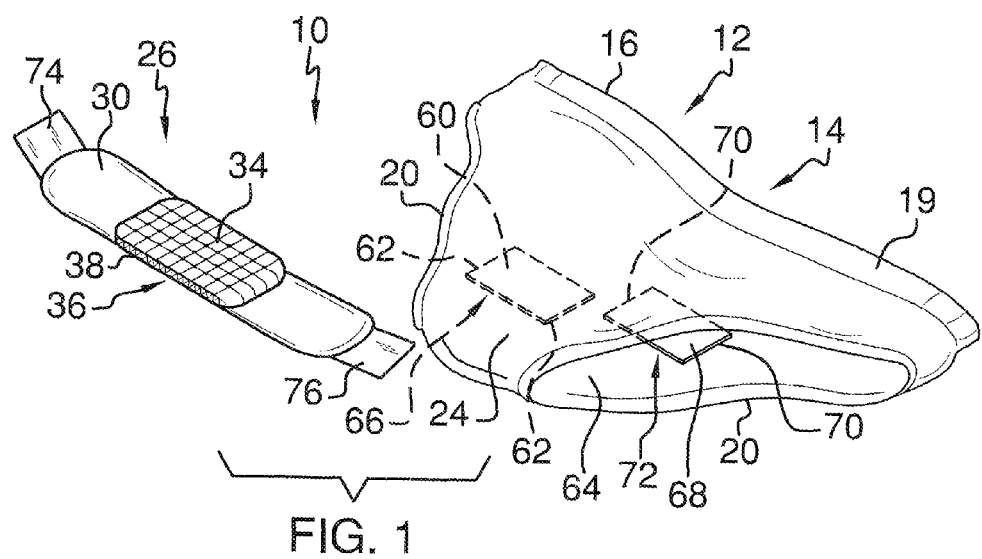
FIG. 1 is a perspective view of a bodily garment assembly according to an embodiment of the disclosure.
Figure 2:
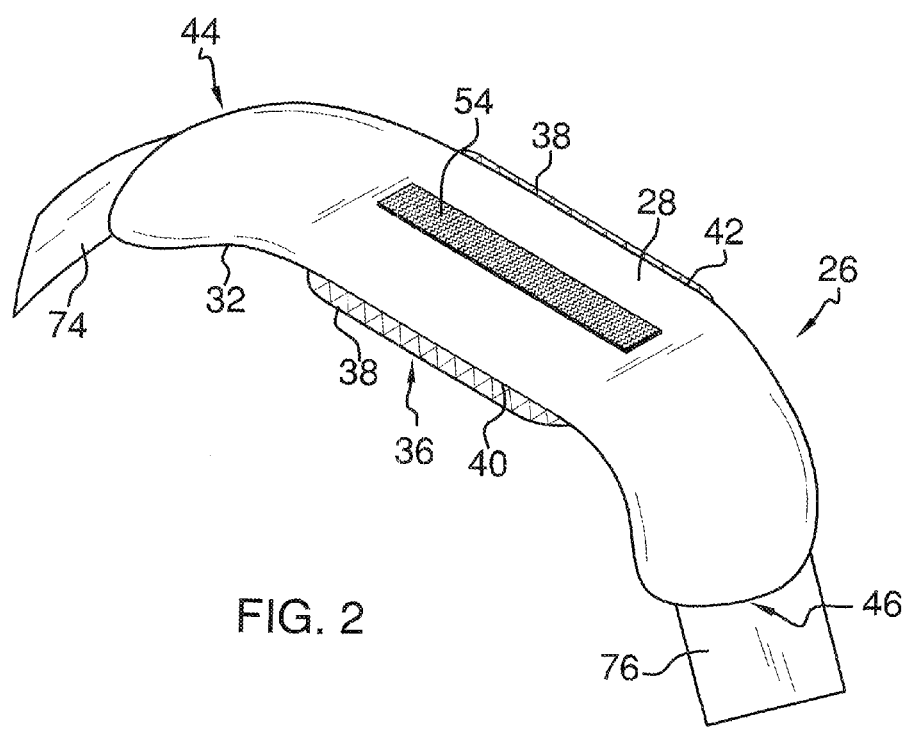
FIG. 2 is a bottom perspective view of an embodiment of the disclosure.
Figure 3:
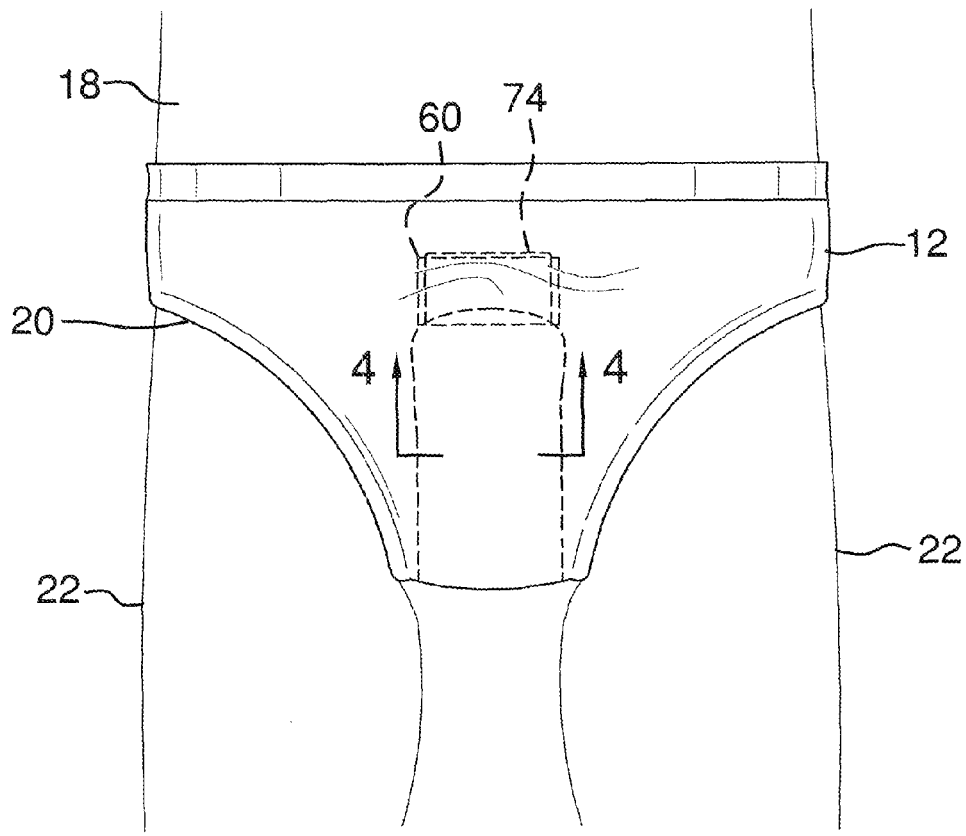
FIG. 3 is a front view of an embodiment of the disclosure.
Figure 4:
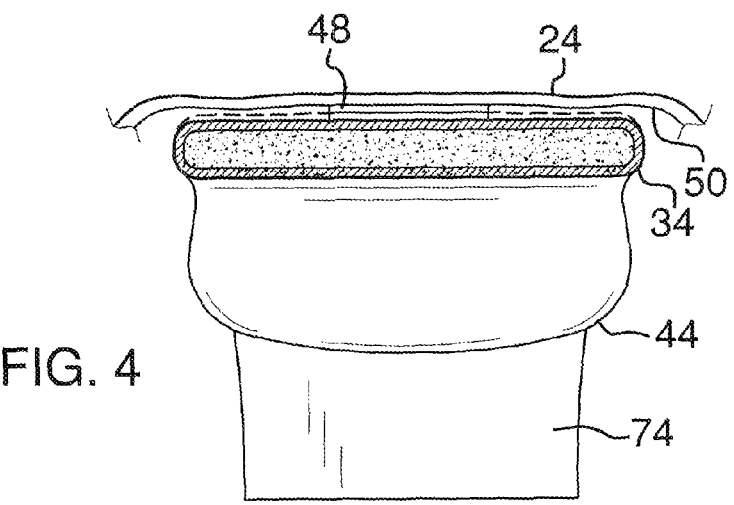
FIG. 4 is a cross-sectional view taken along line 4-4 of an embodiment of the disclosure.

With reference now to the drawings, and in particular to FIGS. 1 through 4 thereof, a new bodily garment device embodying the principles and concepts of an embodiment of the disclosure and generally designated by the reference numeral 10 will be described.

As best illustrated in FIGS. 1 through 4, the bodily garment assembly 10 generally comprises a sleeve 12 that has an open top 14. The open top 14 defines a waistband 16 that may extend around a user's waist 18. The waistband 16 may comprise an elastic band 19. The sleeve 12 has a pair of spaced leg openings 20. Each of the spaced leg openings 20 is positioned on a bottom of the sleeve 12. Each of the spaced leg openings 20 may have an associated one of the user's legs 22 extended therethrough. The sleeve 12 has a crotch section 24. The crotch section 24 is positioned between each of the spaced leg openings 20. The crotch section 24 abuts the user's crotch after each of the user's legs is extended through an associated one of the spaced leg openings 20. The sleeve 12 may be comprised of a deformable material. The crotch section 24 may be comprised of a fluid absorbing material that has a thickness that is greater than a thickness of the sleeve 12.

An absorbing member 26 has a bottom side 28, a top side 30 and a perimeter edge 32. The absorbing member 26 includes a pad 34 that is coupled to a middle portion 36 of the top side 30. The pad 34 may absorb urine. The pad 34 may have a thickness that is greater than the thickness of the absorbing member 26. The pad 34 may be comprised of a fluid absorbing material. The absorbing member 26 has a pair of biasing members 38 coupled to a first lateral side 40 and second lateral side 42 of the perimeter edge 32 proximal the middle portion 36. The biasing members 38 bias a front portion 44 and a rear portion 46 of the absorbing member 26 toward each other so the absorbing member 26 has a U-shape. The biasing members 38 may each comprise an elastic band.

A front panel 60 may be provided having opposite sides 62 coupled to an interior surface 64 of the sleeve 12 defining a front opening 66 facing the crotch section 24 of the sleeve 12. A rear panel 68 has opposite sides 70 coupled to the interior surface 64 of the sleeve 12 defining a rear opening 72 facing the crotch section 24 of the sleeve 12. A front tab 74 is coupled to the absorbing member 26. The front tab 74 may extend from the perimeter edge 32 of the absorbing member 26. A rear tab 76 is coupled to the absorbing member 26. The rear tab 76 may extend from the perimeter edge 32 of the absorbing member 26 opposite the front tab 74 wherein the absorbing member 26 is coupled to the sleeve 12 when the front tab 74 is inserted through the front opening 66 facing the crotch section 24 and the rear tab 76 is inserted through the rear opening 72 facing the crotch section 24.

A mating member 54 is coupled to the bottom side 28 of the absorbing member 26. The mating members 54 frictionally engages an inner surface 50 of the crotch section 24 of the sleeve 12 so the absorbing member 26 is removably retained on the crotch section 24 of the sleeve 12 wherein the pad 34 abuts the user's crotch. The mating member 54 may be an elongated adhesive strip. The absorbing member 26 may be removed from the crotch section 24 and the absorbing member 26 may be disposed of after the pad 34 absorbs a quantity of urine.

In use, the sleeve 12 may be worn by a person to absorb urine if the person involuntarily urinates in their clothing. After urination, the absorbing member 26 may be removed from the sleeve 12 and the absorbing member 26 may be disposed of. The sleeve 12 may be worn with or without having the absorbing member 26 being coupled to the sleeve 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A bodily garment assembly configured to absorb urine, said assembly comprising:

a sleeve configured to be worn around a user's waist whereby said sleeve covers the user's crotch;

an absorbing member, said absorbing member being removably coupled to said sleeve such that said absorbing member is configured to abut the user's crotch, said absorbing member being absorbent such that said absorbing member is configured to absorb urine;

a mating member coupled to a bottom side of said absorbing member, said mating member engaging an inner surface of a crotch section of said sleeve whereby said absorbing member is removably retained on said crotch section of said sleeve such that said pad is configured to abut the user's crotch;

a front panel having opposite sides coupled to an interior surface of said sleeve defining a front opening facing a crotch section of said sleeve;

a rear panel having opposite sides coupled to said interior surface of said sleeve defining a rear opening facing said crotch section of said sleeve;

a front tab coupled to said absorbing member, said front tab extending from a perimeter edge of said absorbing member; and a rear tab coupled to said absorbing member, said rear tab extending from said perimeter edge of said absorbing member opposite said front tab wherein said absorbing member is coupled to said sleeve when said front tab is inserted through said front opening facing said crotch section and said rear tab is inserted through said rear opening facing said crotch section.

2. The assembly according to claim 1, further including said sleeve having an open top, said open top defining a waistband configured to extend around the user's waist.

3. The assembly according to claim 1, further including said sleeve having a pair of spaced leg openings, each of said spaced leg openings being positioned on a bottom of said sleeve, each of said spaced leg openings being configured to have an associated one of the user's legs extended therethrough.

4. The assembly according to claim 3, further including said sleeve having a crotch section, said crotch section being positioned between each of said spaced leg openings wherein said crotch section is configured for abutting the user's crotch after each of the user's legs is extended through an associated one of said spaced leg openings.

5. The assembly according to claim 3, further including said absorbing member having a bottom side, a top side and a perimeter edge, said absorbing member including a pad being coupled to a middle portion of said top side, said pad being configured to absorb urine.

6. The assembly according to claim 5, further including said absorbing member having a pair of biasing members coupled to a first lateral side and second lateral side of said perimeter edge proximal said middle portion, said biasing members biasing a front portion and a rear portion of said absorbing member toward each other whereby said absorbing member has a U-shape.

7. A bodily garment assembly configured to absorb urine, said assembly comprising:

a sleeve, said sleeve having an open top, said open top defining a waistband configured to extend around a user's waist, said sleeve having a pair of spaced leg openings, each of said spaced leg openings being positioned on a bottom of said sleeve, each of said spaced leg openings being configured to have an associated one of the user's legs extended therethrough, said sleeve having a crotch section, said crotch section being positioned between each of said spaced leg openings wherein said crotch section is configured for abutting the user's crotch after each of the user's legs is extended through an associated one of said spaced leg openings;

a front panel having opposite sides coupled to an interior surface of said sleeve defining a front opening facing said crotch section of said sleeve;

a rear panel having opposite sides coupled to said interior surface of said sleeve defining a rear opening facing said crotch section of said sleeve;

an absorbing member, said absorbing member having a bottom side, a top side and a perimeter edge, said absorbing member including a pad being coupled to a middle portion of said top side, said pad being configured to absorb urine, said absorbing member having a pair of biasing members coupled to a first lateral side and second lateral side of said perimeter edge proximal said middle portion, said biasing members biasing a front portion and a rear portion of said absorbing member toward each other whereby said absorbing member has a U-shape;

a front tab coupled to said absorbing member, said front tab extending from said perimeter edge of said absorbing member;

a rear tab coupled to said absorbing member, said rear tab extending from said perimeter edge of said absorbing member opposite said front tab wherein said absorbing member is coupled to said sleeve when said front tab is inserted through said front opening facing said crotch section and said rear tab is inserted through said rear opening facing said crotch section; and a mating member coupled to said bottom side of said absorbing member, said mating member engaging an inner surface of said crotch section of said sleeve whereby said absorbing member is removably retained on said crotch section of said sleeve such that said pad is configured to abut the user's crotch.

* * * * *